US00PP27730P3

(12) United States Plant Patent
Van Dijk

(10) Patent No.: US PP27,730 P3
(45) Date of Patent: Feb. 28, 2017

(54) ***ANTHURIUM* PLANT NAMED 'ANTHDOZAJ'**

(50) Latin Name: ***Anthurium andreanum* L.**
Varietal Denomination: ANTHDOZAJ

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 98 days.

(21) Appl. No.: 14/544,903

(22) Filed: Mar. 6, 2015

(65) Prior Publication Data

US 2016/0270282 P1 Sep. 15, 2016

(51) Int. Cl.
*A01H 5/02* (2006.01)

(52) U.S. Cl.
USPC ..... Plt./366

(58) Field of Classification Search
USPC ..... Plt./366, 365
See application file for complete search history.

(56) References Cited

PUBLICATIONS

Pluto Plant Variety Database 20160723, retrieved on Jul. 26, 2016, retrieved from the Internet at <https://www3.wipo.int/pluto/user/en/index.jsp> one page.*
Anthura Anthurium: Cut flower and pot plant culture, published May 2015, pp. 1-3, 46, 58.
EU Community Plant Variety Rights Application No. 2012/2616, Application n°A201201541, filed Nov. 19, 2012, 7 pages.
EU Community Plant Variety Office Official Gazette, Jan. 2013, Feb. 15, 2013, pp. 1-27, 44, 1, introductory 2 pp.
EU Community Plant Variety Rights Grant No. EU 38416, issued Jun. 16, 2014, 2 pages.

* cited by examiner

*Primary Examiner* — June Hwu
(74) *Attorney, Agent, or Firm* — Jondle & Associates, P.C.

(57) ABSTRACT

A new and distinct variety of *Anthurium* plant named 'ANTHDOZAJ' particularly characterized by having shiny, white, cordate spathes, a white spadix with yellow tip, a high and more spreading plant habit and shiny, dark green foliage, is disclosed.

3 Drawing Sheets

Genus and species: *Anthurium andreanum* L.
Variety denomination: 'ANTHDOZAJ'.

BACKGROUND OF THE NEW PLANT

The present invention comprises a new and distinct variety of *Anthurium*, botanically known as *Anthurium andreanum* L., and hereinafter referred to by the variety name 'ANTHDOZAJ'. The new variety originated from a hybridization made in March 2005 in Bleiswijk, The Netherlands. The female parent is a red *Anthurium* pot plant designated '6727-05' (unpatented), and the male parent was a red *Anthurium* plant designated '7613-01' (unpatented).

A single plant was selected in February 2007 and has been asexually reproduced repeatedly by meristem tissue culture in Bleiswijk, The Netherlands over a five-year period. The present invention has been found to retain its distinctive characteristics through successive asexual propagations.

Plant Breeder's Rights for this variety have been applied for in Europe on Nov. 19, 2012. 'ANTHDOZAJ' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) Shiny, white, cordate spathe;
2) White spadix with yellow tip;

3) High and more spreading plant habit; and
4) Shiny, dark green foliage.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 25-week old plant grown in a greenhouse in Bleiswijk, The Netherlands in February 2015.

DESCRIPTION OF THE NEW VARIETY

Figure 1:
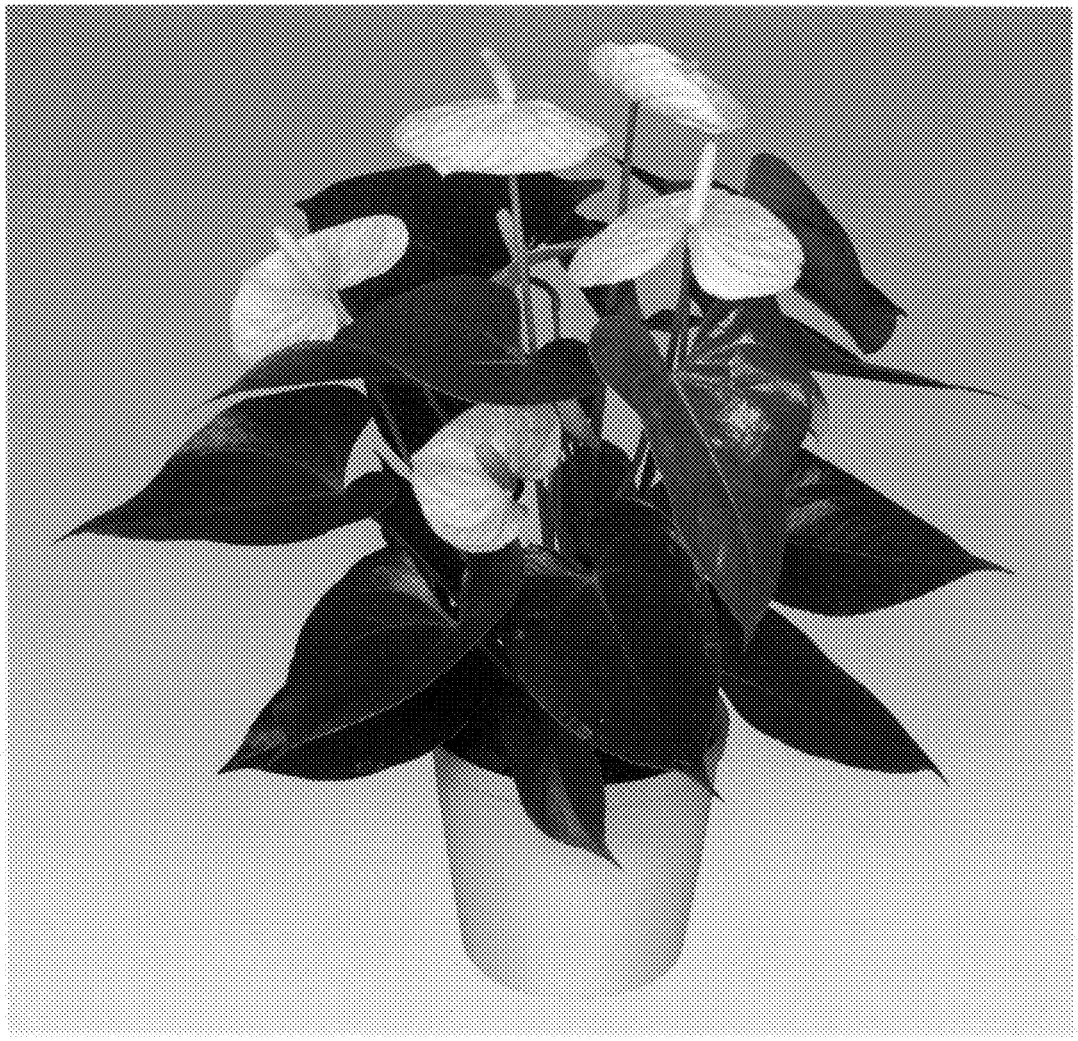
FIG. 1 shows the overall plant habit, including blooms, buds and foliage.
Figure 2:
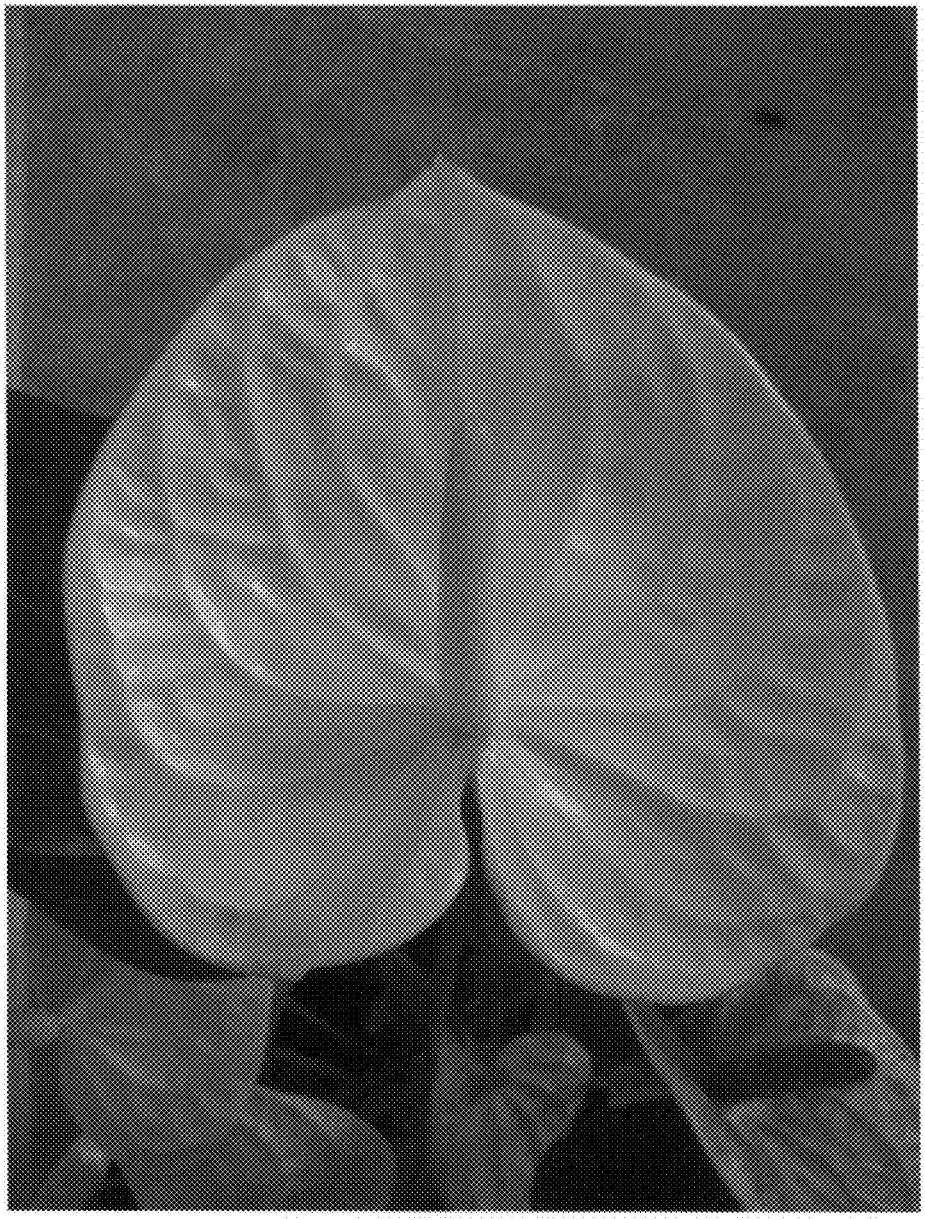
FIG. 2 shows a close-up of the mature spathe.
Figure 3:
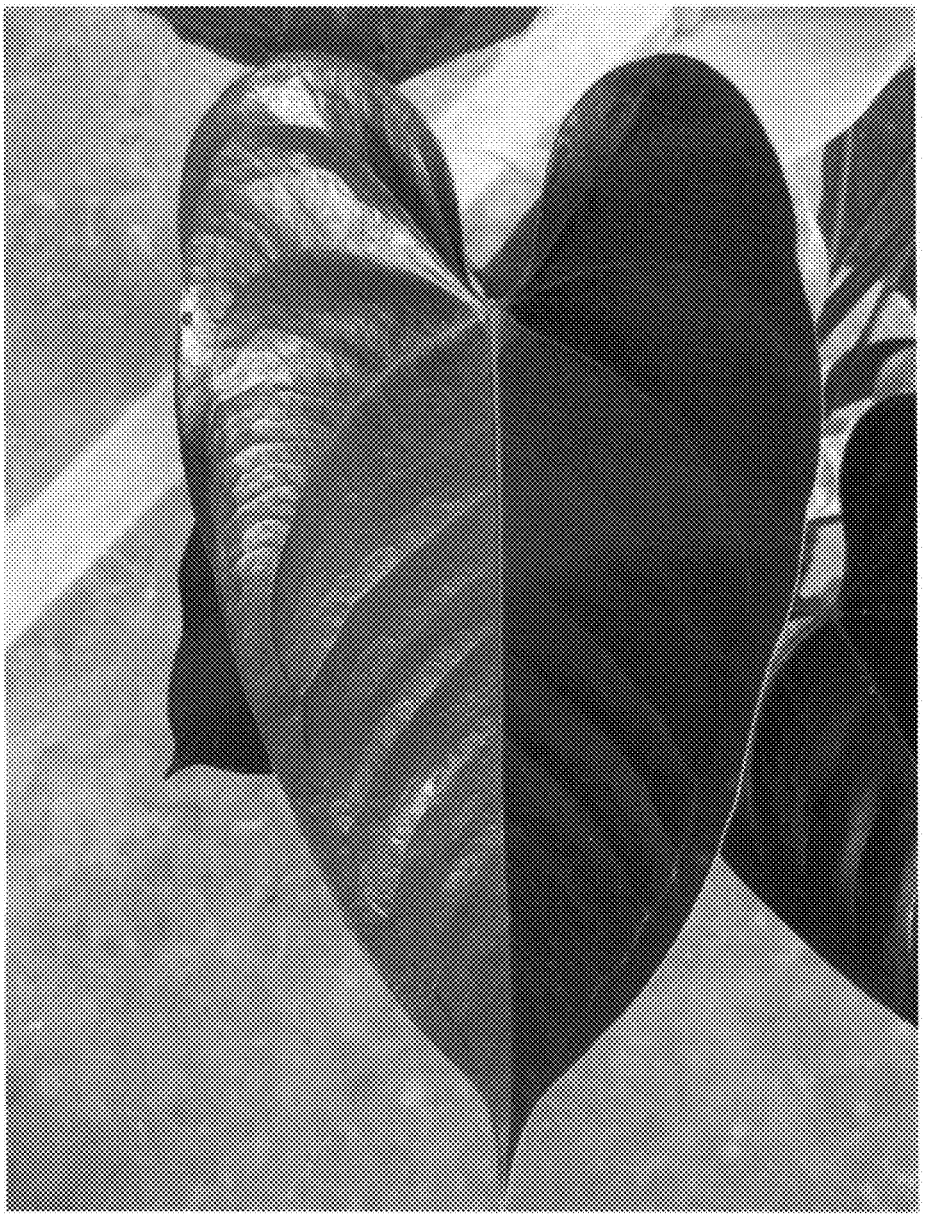
FIG. 3 shows the upper leaf surface.

The following detailed description sets forth the distinctive characteristics of 'ANTHDOZAJ'. The data which define these characteristics were collected from asexual reproductions carried out in Bleiswijk, The Netherlands. The plant history was taken on 25-week old plants which were planted from tissue culture in 17-centimeter pots and grown in a glass greenhouse between 19° C. and 24° C. Observations were made in February 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDOZAJ'.

Parentage:

*Female parent*.—*Anthurium* plant '6727-05' (unpatented).

*Male parent*.—*Anthurium* plant '7613-01' (unpatented).

Plant:

*Propagation*.—Tissue culture.

*Root description*.—Fleshy white-cream colored roots with small hairy lateral roots having yellow-colored root tips.

*Time to produce a finished flowering plant*.—35 to 40 weeks for a 17 cm pot.

*Growth habit*.—Herbaceous perennial.

*Height* (*measured from soil, including inflorescence*).—50.0 cm to 55.0 cm.

*Width* (*measured from leaf tips*).—50.0 cm to 60.0 cm.

Leaves:

*Immature leaves*.—Length: 15.0 cm to 25.0 cm. Width: 9.0 cm to 16.0 cm. Color: Upper surface: RHS 146B. Lower surface: RHS 145A. Texture (both upper and lower surfaces): Shiny.

*Mature leaves*.—Length (fully expanded): 20.0 cm to 30.0 cm. Width: 13.0 cm to 18.0 cm. Shape: Ovate. Apex: Caudate. Base: Cordate. Leaf blade angle with the petiole: Between 105 degrees and 115 degrees. Leaf margin: Entire. Color: Upper surface: RHS 139A. Lower surface: RHS 144A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Arrangement: Leaf blade has two lobes extending past the petiole. The lobes are non-touching. Length of lobes of mature leaf blades: 3.0 cm to 7.0 cm. Width of lobes of mature leaf blades: 5.0 cm to 9.0 cm. Distance from petiole/leaf junction to highest point on lobes of mature leaf blades: 2.0 cm to 4.0 cm.

*Petiole*.—Cross-section: Round. Diameter: 0.3 cm to 0.4 cm. Length: 25.0 cm to 30.0 cm for a mature leaf size. Color: Mature leaf: RHS 144B. Immature leaf: RHS 144B. Cataphyl color surrounding the petiole: Outside: RHS 145A. Inside: RHS 145C.

*Geniculum*.—Length: 3.0 cm to 4.0 cm. Width: 0.4 cm to 0.5 cm. Color: RHS 144B.

Inflorescence:

*Arrangement*.—Single.

*Flowering habit* (*length of flowering season*).—Continuous.

*Number of inflorescences per plant*.—4 to 6.

*Fragrance*.—Absent.

*Longevity of inflorescence on plant*.—Over a year.

*Longevity of the flower as a cut flower*.—45 to 55 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 90 degrees and 120 degrees; the spathe stands on a wiry peduncle about 2.0 cm to 4.0 cm above the foliage.

*Lobe position*.—Free.

*Shape*.—Cordate.

*Apex*.—Broad acuminate.

*Base*.—Cordate.

*Texture*.—Shiny and slightly blistered.

*Margin*.—Entire.

*Size*.—Height: 30.0 cm to 40.0 cm (peduncle length at maturity). Length: 10.5 cm to 12.5 cm. Width: 9.5 cm to 12.5 cm.

*Color*.—Just fully open: Upper surface: RHS 155A. Lower surface: RHS 155A. This white color remains approximately 15 to 25 weeks after opening. After this period the spathe starts greening to RHS 144A.

Peduncle:

*Shape*.—Erect.

*Cross-section*.—Round.

*Length*.—30.0 cm to 40.0 cm.

*Diameter*.—0.3 cm to 0.4 cm.

*Color*.—RHS 145A.

Flowering time:

*General*.—One small rooted untreated tissue culture plant of 2.0 cm tall will flower after 4 to 6 months, depending on the season, and 4 to 6 blossoms will appear. More blossoms appear after some additional weeks so that a full flowering and commercial plant will have 6 to 8 white spathes. Smaller blossoms may occur on less mature plants.

Spadix:

*Size*.—Length: 4.0 cm to 5.0 cm (depending on flower size). Width (at apex): 0.4 cm to 0.5 cm. Width (at base): 0.6 cm to 0.9 cm.

*Shape*.—Columnar.

*Angle from spadix tip to peduncle*.—170 to 180 degrees (spadix is almost in one line with peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 13A. Mature: RHS 159A. Ages to: RHS 144A.

Flowers:

*Quantity per spadix*.—240 to 260.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 159A.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 159A.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHDOZAJ' differs from the female parent plant '6727-05' (unpatented) in that 'ANTHDOZAJ' has a white spathe, whereas '6727-05' has a red spathe.

'ANTHDOZAJ' differs from male parent plant '7613-01' (unpatented) in that 'ANTHDOZAJ' has a white spathe, whereas '7613-01' has a red spathe.

'ANTHDOZAJ' differs from commercial variety 'ANTHCOTBIK' (unpatented) in that 'ANTHDOZAJ' has larger spathe length and width than 'ANTHCOTBIK'.

'ANTHDOZAJ' differs from commercial variety 'ANTHURWAP' (unpatented) in that 'ANTHDOZAJ' has a more blistered spathe than 'ANTHURWAP'. Additionally, 'ANTHDOZAJ' has a yellow spadix when immature, whereas 'ANTHURWAP' has a pink spadix when immature.

I claim:

1. A new and distinct variety of *Anthurium* plant named 'ANTHDOZAJ', substantially as illustrated and described herein.

* * * * *